United States Patent
David et al.

(10) Patent No.: US 8,260,433 B2
(45) Date of Patent: Sep. 4, 2012

(54) APPARATUS AND METHOD FOR APPLYING ENERGY WITHIN AN OBJECT

(75) Inventors: Bernd David, Hamburg (DE); Daniel Wirtz, Hamburg (DE); Oliver Lips, Eindhoven (DE); Steffen Weiss, Hamburg (DE); Sascha Krueger, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 275 days.

(21) Appl. No.: 12/529,366

(22) PCT Filed: Mar. 3, 2008

(86) PCT No.: PCT/IB2008/050769
§ 371 (c)(1),
(2), (4) Date: Sep. 1, 2009

(87) PCT Pub. No.: WO2008/107838
PCT Pub. Date: Sep. 12, 2008

(65) Prior Publication Data
US 2010/0016934 A1    Jan. 21, 2010

(30) Foreign Application Priority Data
Mar. 7, 2007  (EP) ..................... 07103682

(51) Int. Cl.
*A61N 1/00*   (2006.01)
(52) U.S. Cl. ..................... 607/115
(58) Field of Classification Search ............ 607/115
See application file for complete search history.

(56) References Cited

U.S. PATENT DOCUMENTS

| | | | | |
|---|---|---|---|---|
| 3,563,247 A | * | 2/1971 | Bowers | 607/13 |
| 5,167,229 A | * | 12/1992 | Peckham et al. | 607/48 |
| 5,199,429 A | * | 4/1993 | Kroll et al. | 607/5 |
| 5,861,024 A | | 1/1999 | Rashidi | |
| 7,363,090 B2 | * | 4/2008 | Halperin et al. | 607/116 |
| 2002/0116028 A1 | | 8/2002 | Greatbatch et al. | |
| 2003/0204207 A1 | | 10/2003 | MacDonald et al. | |
| 2006/0020297 A1 | | 1/2006 | Gerber | |
| 2006/0106375 A1 | | 5/2006 | Werneth et al. | |

FOREIGN PATENT DOCUMENTS

| | | |
|---|---|---|
| EP | 0090467 A2 | 10/1983 |
| EP | 1488738 A1 | 12/2004 |
| WO | 2005053555 A1 | 6/2005 |
| WO | 2006015938 A1 | 2/2006 |
| WO | 2008032249 A2 | 3/2008 |

OTHER PUBLICATIONS

Nam et al: "Virus-Enabled Synthesis and Assembly of Nanowires for Lithium ION Battery Electrodes": Science May 12, 2006, vol. 312, No. 5775, pp. 885-888.

* cited by examiner

*Primary Examiner* — George Manuel

(57) ABSTRACT

An apparatus for applying energy within an object includes an energy applying unit having an energy emitting element or outputting energy within the object and an energy storage unit locatable within the object and coupled to the energy emitting element. The apparatus further includes an electrical control line coupled to the energy applying unit for controlling the application of energy within the object by controlling transmission of energy from the energy storage unit to the energy emitting element.

16 Claims, 3 Drawing Sheets

APPARATUS AND METHOD FOR APPLYING ENERGY WITHIN AN OBJECT

FIELD OF THE INVENTION

The invention relates to an apparatus, a method and a computer program for applying energy within an object.

BACKGROUND OF THE INVENTION

US2003/0204207 A1 discloses a catheter apparatus comprising a cardiac pacer receiving energy from a battery or a capacitor located at the distal end of a catheter. The transmission of energy from the battery or the capacitor to the cardiac pacer is controlled by an optical control line. The control by an optical control line needs an optical pathway and a conversion device for converting optical signals into electrical signals. These optical and opto-electronical components require a lot of space, wherein the space within the catheter and within a heart is limited. The catheter apparatus is therefore quite large, difficult to manufacture and difficult to handle.

SUMMARY OF THE INVENTION

It is an object of the present invention to reduce the size of an apparatus for applying energy within an object.

In a first aspect of the present invention an apparatus for applying energy within an object is presented, wherein the apparatus comprises:
  an energy applying unit including an energy emitting element for outputting energy within the object and an energy storage unit locatable within the object and coupled to the energy emitting element, and
  an electrical control line coupled to the energy applying unit for controlling the application of energy within the object by controlling a transmission of energy from the energy storage unit to the energy emitting element.

The invention is based on the idea that an optical pathway and a conversion device for converting optical signals to electrical signals are not required, if an electrical control line is used. This reduces the size of the apparatus.

The apparatus for applying energy within an object is, for example, a catheter apparatus for applying energy, for instance, by electrodes located at a distal catheter tip, within the object. The object might be an object of a patient, for example, an organ like a heart of a patient. The energy emitting element can, for example, output energy for ablation or sensing purposes within the object. The object can also be a technical object.

It is preferred that the electrical control line is high resistive. If the electrical control line is high resistive, outer electrical fields are not likely to induce currents in the control line, wherein possible negative effects caused by the induced currents are reduced or no more present. For example, if a magnetic resonance imaging system is used for determining the position of the energy emitting element within the object or for guiding the energy emitting element and the energy storage unit in the object, the electromagnetic radiation, in particular the RF fields, induce only small currents or no currents in the electrical control line, and, thus, a heating, for example, a local heating of the control line, and a disturbance of the imaging by electromagnetic fields generated by the induced currents can be reduced or are not present any more.

It is preferred that the high resistive control line comprises a resistance larger than 2 kOhm/m, further preferred larger than 5 kOhm/m, further preferred larger than 10 kOhm/m and it is further preferred that the resistance is larger than 20 kOhm/m. In particular, these resistances are preferred, if an electrical field, in particular of an magnetic resonance imaging system being preferentially a 1.5 Tesla magnetic resonance imaging system, of preferentially 1 to 10 kV/m, further preferred of 3 to 8 kV/m, further preferred of 5 to 6 kV/m, and further preferred of 5.5 kV/m, preferentially with a frequency of 50 to 80 MHz, further preferred with a frequency of 55 to 70 MHz, further preferred with a frequency of 60 to 65 MHz, further preferred with a frequency of 63 to 64 MHz, and further preferred with a frequency of 63.86 MHz, acts on the control line.

In a preferred embodiment, the apparatus further comprises a control unit coupled with the energy applying unit via the electrical control line for controlling application of energy within the object by controlling a transmission of energy from the energy storage unit to the energy emitting element. The control unit can be located at an arbitrary place as long as it is still coupled with the energy applying unit via the control line. Preferentially, the control unit is located outside of the object, wherein the space needed inside the object by the apparatus for applying energy within an object is further reduced. Thus, preferentially the energy applying unit and the energy storage unit are located at the distal end of the apparatus and the control unit is preferentially located at the proximal end of the apparatus. For example, if the apparatus for applying energy within an object is a catheter apparatus, for instance, for applying energy within an organ of a patient, the energy applying unit and the energy storage unit are preferentially located at the distal end of the catheter and the control unit is preferentially located at the proximal end of the catheter.

It is preferred that the energy applying unit further comprises a switch coupled (a) with the control line for controlling the switch and (b) between the energy emitting element and the energy storage unit for switching the transmission of energy from the energy storage unit to the energy emitting element. This allows switching the energy application with a frequency and an amount of energy needed for the respective application with low technical effort.

It is further preferred that the apparatus comprises a catheter for guiding the energy applying unit, the energy storage unit and the electrical control line into the object. This allows inserting the energy applying unit, the energy storage unit and at least a part of the electrical control line in the object, for example, in an organ of a patient, like a heart of a patient.

The energy storage unit is preferentially rechargeable. This allows using the energy storage unit and, thus, the apparatus for applying energy within the object, for a longer time, without the need for replacing the energy storage unit.

It is preferred that the apparatus further comprises recharge lines, which are connected to the energy storage unit and which are couplable to a recharging unit for recharging the energy storage unit. The recharging unit can be located at an arbitrary place. Preferentially in use the recharging unit is located outside of the object. Thus, the energy storage unit can be recharged by the energy applying unit, while the energy storage unit and at least a part of the electrical control line can remain within the object. In this case, the apparatus preferentially comprises a catheter for guiding the energy applying unit, the energy storage unit, at least a part of the electrical control line and also at least a part of the recharge lines in the object.

The recharge lines are preferentially high resistive, in order to diminish or eliminate effects caused by currents induced in the recharge lines. The recharge lines preferentially have the same resistance as the control line.

It is preferred that the apparatus further comprises a monitoring unit being a magnetic resonance imaging system for monitoring at least one of the energy emitting elements, the energy storage unit and the switch. This allows monitoring at least one of the energy emitting elements, the energy storage unit and the switch, in particular, the position of the at least one of the energy emitting elements, the energy storage and the switch, wherein, for example, the positioning can be corrected using the monitoring result.

The apparatus for applying energy to an object can also comprise a monitoring system for monitoring the position of the energy applying unit within the object. This monitoring unit is, for example, a magnetic resonance imaging system, a computed tomography system, or an ultrasound imaging system.

In a further aspect of the present invention, a method of applying energy within an object is presented, wherein the method comprises the following steps:
applying energy within the object by
locating an energy emitting element and an energy storage unit—coupled to the energy emitting element within the object,
outputting energy within the object by the energy emitting element, wherein the application of energy within the object is controlled by controlling a transmission of energy from the energy storage unit to the energy emitting element by an electrical control line.

In a further aspect of the present invention a computer program for applying energy within an object is presented, wherein the computer program comprises program code means for causing an apparatus to carry out following steps, when the computer program is run on a computer controlling the apparatus:
applying energy within the object by
locating an energy emitting element and an energy storage unit—coupled to the energy emitting element within the object,
outputting energy within the object by the energy emitting element,
electrically controlling the application of energy within the object by controlling a transmission of energy from the energy storage unit to the energy emitting element by an electrical control line.

It shall be understood that the apparatus of claim 1, the method of claim 9 and the computer program of claim 10 have similar and/or identical preferred embodiments as defined in the dependent claims. It shall be understood that preferred embodiments of the invention can also be any combination of the dependent claims.

BRIEF DESCRIPTION OF THE DRAWINGS

These and other aspects of the invention will be apparent from and elucidated with reference to the embodiments described hereinafter. In the following drawings.

DETAILED DESCRIPTION OF EMBODIMENTS

Figure 1:
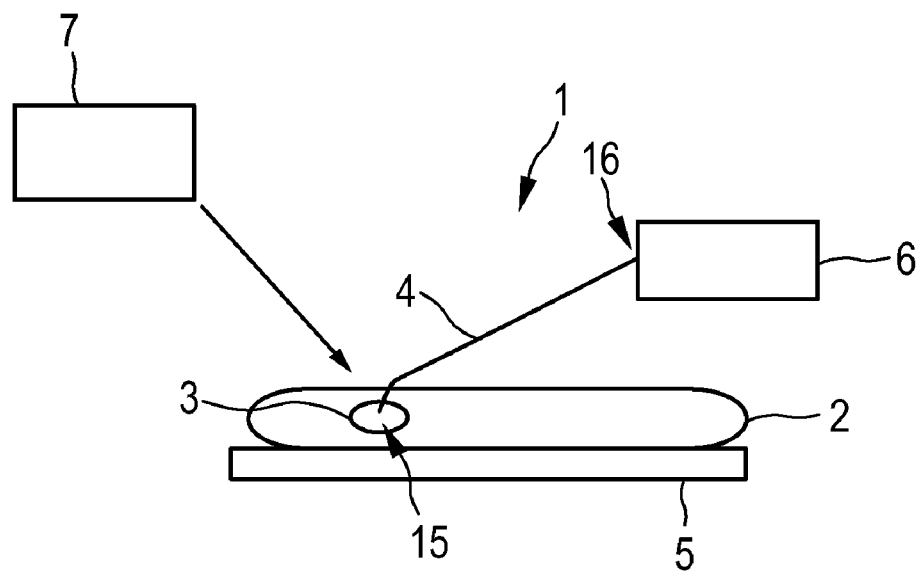
FIG. 1 shows schematically an embodiment of an apparatus for applying energy within an object.
Figure 2:
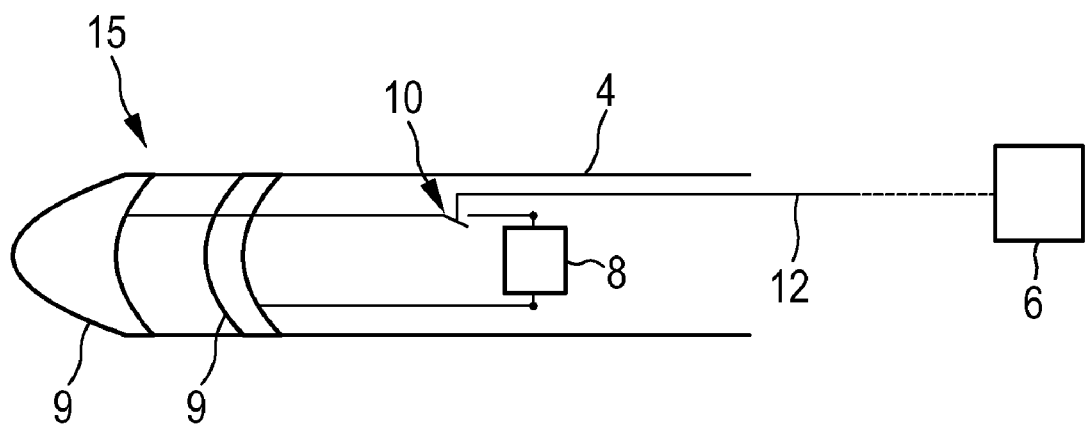
FIG. 2 shows schematically and in more detail a distal end of a catheter of the apparatus for applying energy within an object.

FIG. 1 shows schematically an apparatus for applying energy within an object, which is in this embodiment a catheter apparatus 1. The catheter apparatus 1 comprises a catheter 4 having a distal end 15 and a proximal end 16. The distal end of the catheter is shown in more detail schematically in FIG. 2. At the distal end 15 of the catheter 4 two energy emitting elements 9 for outputting energy within the object 2, 3 and an energy storage unit 8 are located. In this embodiment, the energy emitting elements 9 are energy emitting electrodes, in particular for sensing or ablation procedures. The energy storage unit 8 is in this embodiment a battery. In this embodiment the energy emitting elements are pacing electrodes. The energy emitting elements 9 are coupled to the energy storage unit 8 via a switch 10. The switch 10 is coupled to a control unit 6 via an electrical control line 12. In this embodiment, the control unit 6 is located outside of the object 2, 3 at the proximal end of the catheter 4. The electrical control line 12 has certainly to be long enough to reach the control unit 6 outside of the object 2, 3. This length of the electrical control line is illustrated in FIG. 2 by the broken line.

The object 2, 3 is in this embodiment a heart 3 of a patient 2. Thus, in the situation shown in FIG. 1, the distal end 15 of the catheter 4 including the energy emitting element 9, the energy storage unit 8 and the switch 10 have been inserted into the heart 3 of the patient 2. The patient 2 is located on a patient table 5. The apparatus 1 further comprises a monitoring unit 7 for monitoring at least one of the energy emitting elements 9, the energy storage unit 8 and the switch 10. In this embodiment, the monitoring unit 7 is a magnetic resonance imaging system.

Figure 3:
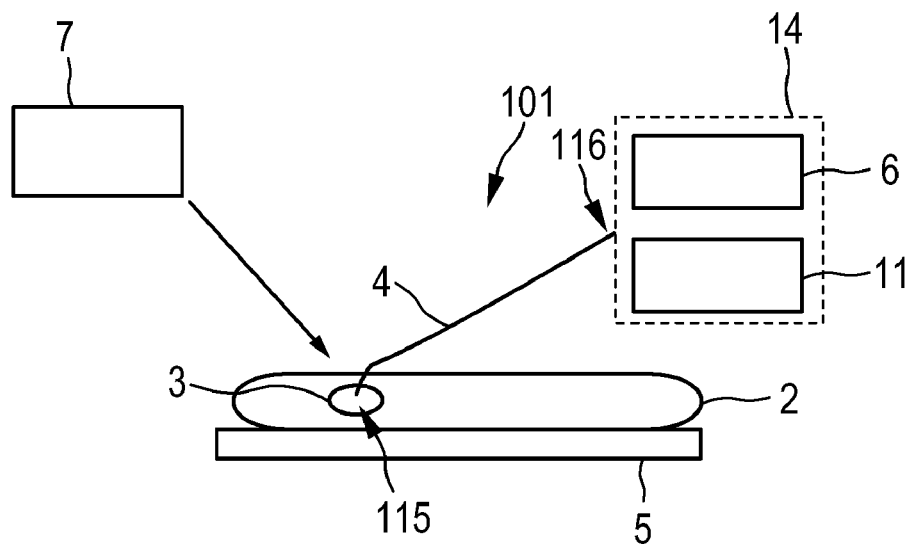
FIG. 3 shows schematically a further embodiment of an apparatus for applying energy within an object.

FIG. 3 shows schematically another embodiment of an apparatus 101 for applying energy within an object. Elements, which are similar to the elements shown in FIG. 1, are denoted by similar reference numbers and will in the following not be explained again in detail.

The apparatus 101 comprises a control and recharge device 14, which includes the control unit 6 and a recharging unit 11. The control and recharging device 14 is coupled to the catheter 4, in particular the control unit 6 is coupled to an electrical control line 12 and the recharging unit 11 is coupled to an electrical recharge line 13, as it is schematically shown in FIG. 4.

Figure 4:
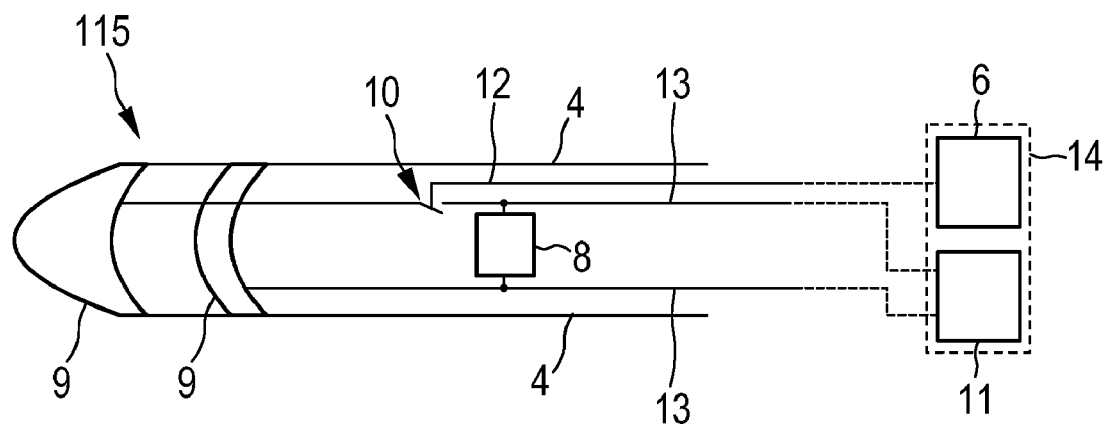
FIG. 4 shows schematically a distal end of a catheter of the further embodiment of the apparatus for applying energy within an object.

The distal end 115 of the catheter 4 is schematically shown in FIG. 4.

In the embodiment shown in FIG. 4, the energy storage unit 8 is coupled to the recharging unit 11 via recharge lines 13. In this embodiment, the recharging unit 11 is located outside of the object 2, 3 and, therefore, the recharge lines 13 have to be sufficient long. This large length is illustrated in FIG. 4 schematically by broken lines.

The energy emitting elements 9, the energy storage unit 8 and the switch 10 form an energy applying unit which is controllable by a control unit via an electrical control line.

Figure 5:
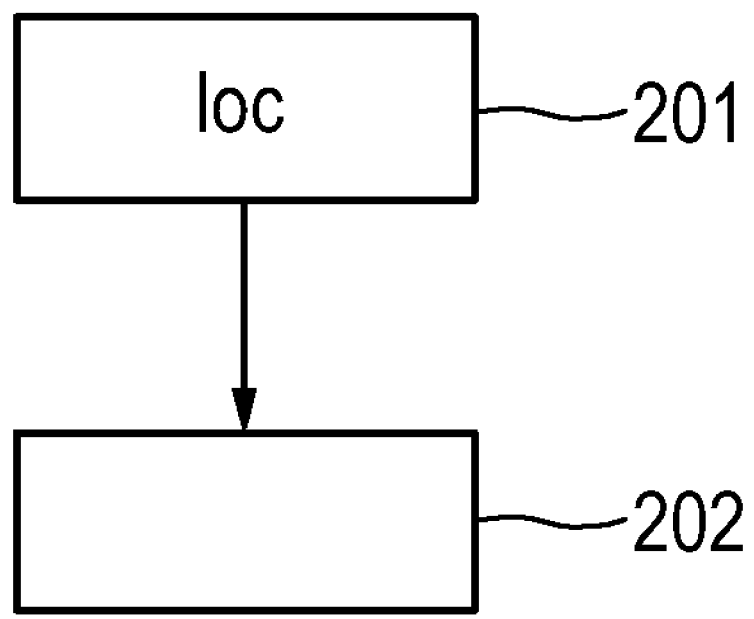
FIG. 5 shows a flowchart illustrating an embodiment of a method for applying energy within an object.

In the following an embodiment of a method for applying energy within an object will be described with reference to a flowchart shown in FIG. 5.

In step 201, the distal end 15, 115 of the catheter 4 is located within the object 2, 3, i.e. within the heart 3 of the patient 2 in this embodiment. In particular, the energy emitting elements 9 are located at a desired position within the object 2, 3, at which energy should be applied.

In step 202 energy is outputted by the energy emitting element at the position, at which the energy emitting element has been located, wherein the emission of energy, i.e. the application of energy within the object, is controlled by controlling a transmission of energy from the energy storage unit 8 to the energy emitting elements 9 by the electrical control line 12. In this embodiment, the switch 10 is controlled by the control unit 6 via the electrical control line 12 for controlling the transmission of energy from the energy storage unit 8 to the energy emitting elements 9.

In the embodiment shown in FIG. 3, the energy storage unit 8 can be recharged by connecting the energy storage unit 8 with the recharging unit 11 via the recharge lines 13. The recharge lines 13 are preferentially high resistive lines, and therefore, the energy storage unit 8 can be recharged, even if the position of the energy emitting elements 9 is still monitored by the electromagnetic resonance imaging system 7. Thus, the energy storage unit 8 can be recharged during, for example, an electrophysiology intervention.

Also the electrical control line is preferentially high resistive in order to allow magnetic resonance imaging while the energy emitting elements 9 and the energy storage unit 8 are still located within the object 2, 3.

The use of high resistive lines allows performing electro physiology interventions under magnetic resonance guidance without the risk of RF heating, because the electrical connection to the energy applying unit at the catheter tip, which is placed inside the object, during the electrophysiology intervention cannot become resonant at the operating frequency of the magnetic resonance imaging system and, thus, cannot act as an antenna for the applied RF fields, which would lead to excessive heating. The energy emitting elements are in particular cardiac pacing electrodes.

Since the energy, which has to be applied within the object, is stored in an energy storage unit adjacent to the energy emitting elements, the electrical control line, which leads to a control unit preferentially outside of the object, i.e. at the proximal end of the catheter, only needs to control the switch and, thus, can be a high resistive electrical connection.

The energy storage unit can be a capacitor, a battery or an accumulator, preferable a miniaturized Li-Ion or Li-polymer battery, which preferentially fits into the distal lumen of a catheter. Several energizing units, i.e. for example a capacitor, a battery and/or an accumulator, can be connected in series, in order to increase the possible voltage, i.e. the energy, applied within the object.

If the electrical control line is high resistive, energy can be applied in a controlled manner within an object, while the position of the energy emitting element is monitored, by using a magnetic resonance imaging system, i.e. an X-ray system for monitoring is not required, wherein radiation and also contrast agent dose applied to the object, which is preferentially a patient, can be avoided. The use of high resistive electrical control lines and preferentially of high resistive recharge lines overcomes the inherent safety risk of regular electrophysiology instruments and devices and thus provides a solution for magnetic resonance safe intracardial transcatheter pacing for magnetic resonance guided electrophysiology interventions.

If the apparatus for applying energy within an object is a catheter apparatus for an electrophysiology cardiac application and if the energy emitting elements are pacing electrodes, the pacing signals consist of current pulses of preferentially 1 to 30 mA at pulse length of preferentially 1 to 10 ms at repetition rates of preferentially 0.6 to 6 Hz. The energy needed for approx. 1000 pulses is preferentially about 1 Ws, if a preferred voltage of 2.8 V is assumed as typically used in a pacemaker. Preferentially the energy storage unit is able to store about 1 Ws in the small lumen of the catheter tip (some cubic millimeters) at the distal end of the catheter.

As already mentioned above, the energy storage unit can be a single or a combination of Li-Ion and Li-polymer batteries and accumulators. In particular, the batteries and accumulators used in handheld devices as cell-phones, digital cameras and video cameras can be used, preferentially if they are small enough for fitting in the small lumen of a catheter tip. Also Li-Ion batteries, which are generally used in a pacemaker, can be used, preferentially if their size is small enough to fit in the small lumen of a catheter tip. Also thin-film, flexible, nanoscale Li-Ion batteries, as for example disclosed in "Virus-Enabled Synthesis and Assembly of Nanowires for Lithium Ion Battery Electrodes", Ki Tae Nam et al., Science 12 May 2006: Vol. 312. no. 5775, pp. 885-888, can be used as the energy storage unit. Preferentially, the energy storage unit comprises one or a combination of batteries, such that it supplies a voltage of up to 40 V which is typical for external pacing power supplies.

Although in the preferred embodiment the apparatus for applying energy within an object has been used for applying energy within a patient, in particular within a heart of a patient, the invention is not limited to the application of energy within a patient, in particular not to an application within a heart. Energy can also be applied within another organ of a patient or within a lumen of a technical object.

Although the invention has been described as comprising a monitoring unit for monitoring the position of the energy emitting elements within the object, the invention is not limited to an apparatus for applying energy within an object having a monitoring unit. Furthermore, if a monitoring unit is present, this monitoring unit has not to be a magnetic resonance imaging system. Also other monitoring units could be used for monitoring the position of the energy emitting elements within the object, for example, an X-ray imaging system like an X-ray projection system.

Although in FIGS. 2 and 4 only several parts within the catheter have been shown, the catheter can also comprise more components, in particular components, which are generally used within a catheter as for instance a guide wire, additional wires to electrodes at the catheter tip or extra lumina to deliver cryo fluids to the catheter tip.

Other variations to the disclosed embodiments can be understood and effected by those skilled in the art and practicing the claimed invention from the study of the drawings, the disclosure and the appended claims.

While the invention has been illustrated and described in detail in the drawings and in the foregoing description, such illustration and description are to be considered illustrative or exemplary and not restrictive. The invention is not limited to the disclosed embodiments.

In the claims the word "comprising" does not exclude other elements or steps and the indefinite article "a" or "an" does not exclude a plurality.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the internet or other wired or wireless telecommunication systems.

Any reference signs in the claims should not be construed as limiting the scope.

The invention claimed is:

1. An apparatus for applying energy within an object of a patient, wherein the apparatus comprises:
   an energy applying unit for insertion in the patient and comprising an energy emitting element for outputting energy within the object, and an energy storage unit coupled to the energy emitting element, the energy applying unit being positionable within the object of the patient;
   an electrical control line coupled to the energy applying unit for controlling the application of energy within the object by controlling a transmission of energy from the energy storage unit to the energy emitting element; and
   a switch coupled with the electrical control line for controlling the switch,
   wherein the energy storage unit comprises a battery, the energy emitting element comprises electrodes, and the switch is connected between the electrodes and the battery for switching the transmission of energy from the battery to the electrodes, and
   wherein a resistance per unit of length of the electrical control line is larger than 2.0 kOhm/m.

2. The apparatus as claimed in claim 1, further comprising a control unit coupled with the energy applying unit via the electrical control line for controlling application of energy within the object by controlling the transmission of energy from the energy storage unit to the energy emitting element.

3. The apparatus as claimed in claim 1, wherein the switch is connected between the electrodes and the battery.

4. The apparatus as claimed in claim 1, further comprising a catheter for guiding the energy applying unit, the energy storage unit and the electrical control line into the object.

5. The apparatus as claimed in claim 1, wherein the energy storage unit is rechargeable.

6. The apparatus as claimed in claim 5, further comprising recharge lines which are connected to the energy storage unit and which are couplable to a recharging unit for recharging the energy storage unit.

7. The apparatus as claimed in claim 6, wherein a resistance per unit of length of the recharge lines is larger than 2.0 kOhm/m.

8. The apparatus as claimed in claim 1, further comprising a monitoring unit including a magnetic resonance imaging system for monitoring at least one of the energy emitting element, the energy storage unit and the switch.

9. The apparatus of claim 1, wherein the electrical control line is configured to minimize induced currents induced in the electrical control line by an imaging system, and wherein the imaging system comprises one of a magnetic resonance imaging system, a computed tomography system, and an ultrasound imaging system for at least one of determining a position of the energy emitting element within the object and guiding the energy emitting element and the energy storage unit in the object.

10. The apparatus of claim 1, wherein the electrical control line is configured to prevent becoming resonant at an operating frequency of an imaging system.

11. The apparatus of claim 10, wherein the imaging system comprises
   a magnetic resonance imaging system for at least one of determining a position of the energy emitting element within the object and guiding the energy emitting element and the energy storage unit in the object.

12. The apparatus of claim 1, wherein the induced currents are induced in the electrical control line by electromagnetic radiation from the imaging system.

13. The apparatus of claim 1, wherein the transmission of energy from the energy storage unit to the energy emitting element is performed only by controlling the switch.

14. The apparatus of claim 1, further comprising a controller for controlling the switch by the electrical control line, wherein the controller is located at a proximal end of the apparatus, and wherein the energy emitting element, an energy storage unit, and the switch are located at a distal end of the apparatus.

15. A method for applying energy within an object of a patient comprising the act of:
   applying energy within the object locating within the object of the patient an energy applying unit comprising an energy emitting element and an energy storage unit, the energy storage unit being coupled to the energy emitting element; and
   outputting energy within the object by the energy emitting element, wherein the outputting of the energy within the object is controlled by controlling a transmission of energy from the energy storage unit to the energy emitting element by an electrical control line,
   wherein the energy storage unit comprises a battery, the energy emitting element comprises electrodes, and a switch is coupled with the electrical control line for controlling the switch, and wherein the switch is connected between the electrodes and the battery for switching the transmission of energy from the battery to the electrodes, and
   wherein a resistance per unit of length of the electrical control line is larger than 2.0 kOhm/m.

16. A non-transitory computer readable medium embodying program code when run on a processor, configures the processor to perform the act of:
   applying energy within an object of a patient by locating within the object of the patient an energy applying unit comprising an energy emitting element and an energy storage unit, the energy storage unit being coupled to the energy emitting element;
   outputting energy within the object by the energy emitting element; and
   electrically controlling the outputting of the energy within the object by controlling a transmission of energy from the energy storage unit to the energy emitting element by an electrical control line,
   wherein the energy storage unit comprises a battery, the energy emitting element comprises electrodes, and a switch is coupled with the electrical control line for controlling the switch, and wherein the switch is connected between the electrodes and the battery for switching the transmission of energy from the battery to the electrodes, and
   wherein a resistance per unit of length of the electrical control line is larger than 2.0 kOhm/m.

* * * * *